US006432658B1

(12) United States Patent
Hoogendoorn et al.

(10) Patent No.: US 6,432,658 B1
(45) Date of Patent: Aug. 13, 2002

(54) METHOD FOR MEASURING ANTITHROMBIN ACTIVITY

(75) Inventors: Hugh W. Hoogendoorn, Ancaster (CA); Alexander Duncan, Decatur, GA (US); Michael J. Morris, South Bend, IN (US)

(73) Assignees: Affinity Biologicals, Inc., Hamilton (CA); R2 Diagnostics, Inc., South Bend, IN (US)

( * ) Notice: Subject to any disclaimer, the term of this patent is extended or adjusted under 35 U.S.C. 154(b) by 52 days.

(21) Appl. No.: 09/661,142

(22) Filed: Sep. 13, 2000

(51) Int. Cl.[7] .............................. C12Q 1/56; C12Q 1/00; C12Q 1/37

(52) U.S. Cl. .............................. 435/13; 435/4; 435/23; 435/975

(58) Field of Search .............................. 435/13, 4, 23, 435/975

(56) References Cited

U.S. PATENT DOCUMENTS

| | | | |
|---|---|---|---|
| 4,106,990 A | 8/1978 | Karges et al. | 195/63 |
| 4,139,415 A | 2/1979 | Yin et al. | 195/103.5 |
| 4,948,724 A | 8/1990 | Yin | 435/13 |
| 5,051,357 A | 9/1991 | Hassouna | 435/13 |
| 5,093,237 A | 3/1992 | Enomoto | 435/13 |
| 5,221,614 A | 6/1993 | Enomoto | 435/13 |
| 5,443,960 A | 8/1995 | Dahlbäck | 435/13 |
| 5,525,478 A | 6/1996 | Matschiner | 435/13 |
| 5,716,795 A | 2/1998 | Matschiner | 435/13 |
| 5,780,255 A | 7/1998 | Preda | 435/23 |
| 6,090,570 A | * 7/2000 | Kraus | 435/13 |

OTHER PUBLICATIONS von Kaulla, E., von Kualla, K.: Antithrombin III and Diseases. Amer. J. Clin. Path. 48; 69–80 (1967).

Abildgaard, U., Gravem, K., Godal, H.C.: Assay of Progressive Antithrombin in Plasam. Thromb. Diath. Haemorrh., 24; 224–229 (1970).

Hoogendoorn, H., Cerskus, A., Ofosu F, Blajchman, M., Hirsh, J.; Preparation and Partial Characterization of Human Plasma Depleted of Antithrombin–III by Heparin–Sepharose Affinity Chromatography. Thrombosis Research, 20; 77–83 (1980).

Holmer E., Söderström G., Andersson L. –O: Properties of Antithrombin III Depleted Plasma. I. Effect of Heparin. Thrombosis Research 17; 113–124 (1980).

Odegard, O.R., Lie, M., Abildgaard, U.: Antifactor Xa Activity Measured with Amidolytic Methods. Haemostasis 5; 265–275 (1976).

Odegard, O.R., Abildgaard, U.: Antithrombin III: Critical Review of Assay Methods. Significance of Variations in Health and Disease. Haemostasis 7: 127–134 (1978).

Nordfang, O., Kristensen, H.I., Valentin. S., Ø̸stergaard, P., Wadt, J.: The Significance of TFPI in Clotting Assays—Comparison and Combination with other Anticoagulants. Thrombosis and Haemostasis 70: (3) 448–453 (1993).

(List continued on next page.)

Primary Examiner—Louise N. Leary
(74) Attorney, Agent, or Firm—Kolisch Hartwell Dickinson McCormack & Heuser

(57) ABSTRACT

The invention provides a one-stage method of measuring antithrombin (AT) activity in a sample. In the method, a diluted sample is mixed with AT-deficient plasma containing intrinsic coagulation enzymes, an AT augmenting compound such as heparin, a phospholipid and an activator of the contact phase of the intrinsic coagulation pathway. Following addition of calcium ions, coagulation time is measured and compared to a reference standard to determine the level of AT activity in the sample.

38 Claims, 1 Drawing Sheet

AT-C comparison to Chromogenix-AT

- Normal range = 82-130 %
- $R^2 = 0.91$
- AT-C performed on an optical endpoint instrument (MDA-180)
- Intra-assay CV = 6.1 %
- Inter-assay CV = 9.9 %
- Chromogenix-AT performed on Cobas-Fara instrument

OTHER PUBLICATIONS

Marciniak, E.: Adverse Effect of Heparin on Thrombin Inactivation. Thromb et Diathesis Haemorrhagica 34; 365 (1975).

Downing, M., Bloom, J.W., Mann, K.G.: Comparison of the Inhibition of Thrombin by Three Plasma Protease Inhibitors. Biochemistry 17; 2649–2653 (1978).

Bohner, J., von Pape, K–W., Blaurock, M.: Thrombin–Based Antithrombin–Based Antithrombin Assays Show Over–Estimation of Antithrombin III Activity in Patients on Heparin Therapy due to Heparin Cofactor II Influence. Thrombosis and Haemostatsis 71; 280–283 (1994).

Jesty, J.: Analysis of the Generation and Inhibition of Activated Coagulation Factor X in Pure Systems and in Human Plasma. J Biol Chem 19; 8695–8702 (1986).

Pier Mannuccio Mannucci and Armando Tropodi: Laboratory Screening of Inherited Thrombotic Syndromes. Thrombosis and Haemostasis 57 (3) 247–251 (1987).

Cosgriff, T.M., Hershgold, E.J., Martin, B.A., Calson, K.S.: False Assignment of Familial Antithrombin III Deficiency with the von Kaulla Assay: Am J Clin Path 80: 697–699 (1983).

Gitel, S.N., Wessler. S.: Plasma Antithrombin III: A Quantitative Assay of Biological Activity. Thrombosis Research 7; 5–16 (1975).

Thrombotek PC Product Direction Insert dated Sep. 1996.

ProC™ Global Direction Insert.

* cited by examiner

AT-C comparison to Chromogenix-AT

- Normal range = 82-130 %
- $R^2 = 0.91$
- AT-C performed on an optical endpoint instrument (MDA-180)
- Intra-assay CV = 6.1 %
- Inter-assay CV = 9.9 %
- Chromogenix-AT performed on Cobas-Fara instrument

US 6,432,658 B1

METHOD FOR MEASURING ANTITHROMBIN ACTIVITY

FIELD OF INVENTION

This invention relates to a method of measuring antithrombin activity.

BACKGROUND OF INVENTION

Blood coagulation or clotting results when a series of inactive enzymes in blood are activated to generate, at the end of the cascade, a clot at the site of the wound. The intrinsic blood coagulation pathway is activated upon contact with the surface of a foreign matter which initiates the sequential activation of factors XII to XIIa, prekallikrein to kallikrein, kininogen to kinin, XI to XIa, IX to IXa, X to Xa, and II (prothrombin) to IIa (thrombin). Tissue thromboplastin initiates the extrinsic blood coagulation pathway by activation of factor X, which in turn results in the activation of prothrombin to form thrombin. In both pathways, the final enzyme in the cascade is thrombin, a serine protease which cleaves the soluble protein fibrinogen to form fibrin. Fibrin molecules crosslink to form a clot which reduces the flow of blood from the wound.

Antithrombin or antithrombin III (AT) is an important regulator of blood coagulation. AT, which is produced in the liver, is a serine protease inhibitor with a molecular weight of approximately 60,000 Daltons and circulates in the blood at a concentration of 150 to 200 micrograms per milliliter, or 2.5 to 3.4 micromoles per liter. AT has a broad specificity, and inhibits most of the coagulation factors involved in the intrinsic and the extrinsic pathways and is the principle regulator of thrombin. The inhibition of most coagulation enzymes by AT is significantly augmented in the presence of heparin.

AT deficiency is associated with an increased risk of thrombosis. The condition may be congenital, or acquired as a result of underlying conditions such as liver disease, kidney disease or disseminated intravascular coagulation. AT deficiency may be related to reduced levels of AT or reduced AT activity. For example, in congenital AT deficiency type II, the AT concentration is normal but the activity is reduced due to the presence of a dysfunctional AT. Successful clinical diagnosis and management of patients with AT deficiency therefore demands a specific, sensitive and a simple laboratory assay of the AT activity.

Current methods to determine AT deficiency can be divided into three classes: immunoassays, amidolytic-based activity assays and clot-based activity assays.

Immunoassay techniques measure the concentration of AT in a sample through methods such as radial immunodiffusion, nephelometry and enzyme-linked immunosorbant assays (ELISAs). These assays are very specific and quite sensitive, but can be time-consuming to perform. As well, concentration measurements of AT do not always correlate with AT activity levels since inactive forms of AT or AT-enzyme complexes may still exhibit immunoreactivity in these assays. This may lead to inappropriately high test results for some patients with reduced AT activity as in the case of type II deficiency.

Amidolytic-based activity assays work on the principle of incubating a fixed quantity of a single purified enzyme, usually thrombin or factor Xa, with a diluted test sample and heparin. The residual enzyme activity is measured by determining the endpoint or kinetic rate of cleavage of synthetic chromogenic or fluorogenic substrates. These types of assays are currently the most widely used methods to determine AT activity levels. However, these assays tend to be susceptible to interference from other coagulation inhibitors such as $\alpha_2$-macroglobulin, heparin cofactor II and $\alpha_1$-antitrypsin. As well, measurements of AT activity vary depending on which purified enzyme is used for the assay. Costs for these assays can be fairly high due to the use of purified enzymes and synthetic substrates, and the requirement for a spectrophotometer or high-end coagulation analyser to detect the reaction endpoint.

Clot-based activity assays may be performed as either two-stage or one-stage assays. The two-stage assays involve incubating a fixed quantity of purified enzyme, such as thrombin, with defibrinated test serum or plasma. Residual enzyme activity is measured by determining clotting activity upon the addition of plasma or purified fibrinogen instead of determining the amidolytic activity as described above. Drawbacks of these assays include artifactual reduction of AT levels if heat denaturation is used to defibrinate the plasma. Also, these methods tend to be cumbersome and labour intensive, time-consuming, and susceptible to interference by other progressive coagulation inhibitors.

A one-stage clot-based assay is described in U.S. Pat. No. 5,093,237 to Enomoto. In this assay, the test specimen is mixed with AT-free plasma containing the extrinsic coagulation factors, heparin and a prothrombin time measuring reagent and the coagulation time resulting from the activation of the extrinsic coagulation pathway is measured. The prothrombin time test is known to be extremely insensitive to heparin-enhanced inhibition by AT and the Enomoto assay discloses the use of a high concentration of heparin (12 U/ml). This is far above the optimal concentration of heparin for AT and at such high concentrations, it is known that the efficiency of inhibition by AT is reduced. Moreover, while Enomoto discloses that the extrinsic coagulation reaction is utilized to avoid the many potential errors in the intrinsic reaction pathway, the assay generates only two enzymes, activated Factor X and thrombin, upon which AT can exert its inhibitory effect and does not best reflect the full spectrum of in vivo physiological AT activity.

It is apparent therefore, that there remains to be developed a sensitive, specific yet simple clot-based laboratory assay for AT activity.

SUMMARY OF INVENTION

The present invention provides a method for measuring AT activity in samples containing AT, such as in a patient plasma sample. The method of the invention includes the step of mixing a test sample with an AT-deficient substrate plasma, an activator of the contact phase of the intrinsic coagulation pathway and a phospholipid. The AT-deficient plasma contains the enzymes of the intrinsic coagulation pathway and may also contain an AT augmenting compound, such as heparin. The AT augmenting compound if not present in the substrate plasma is added separately to the test sample. Following addition of calcium ions to the mixture, the coagulation time is measured. By comparing the coagulation time to a reference standard, the AT activity level of the test sample can be determined.

In another aspect, the invention provides a kit for measuring AT activity which kit includes an AT-deficient substrate plasma, an AT augmenting compound, an APTT reagent and a calcium salt solution.

DETAILED DESCRIPTION OF THE INVENTION

Figure 1:
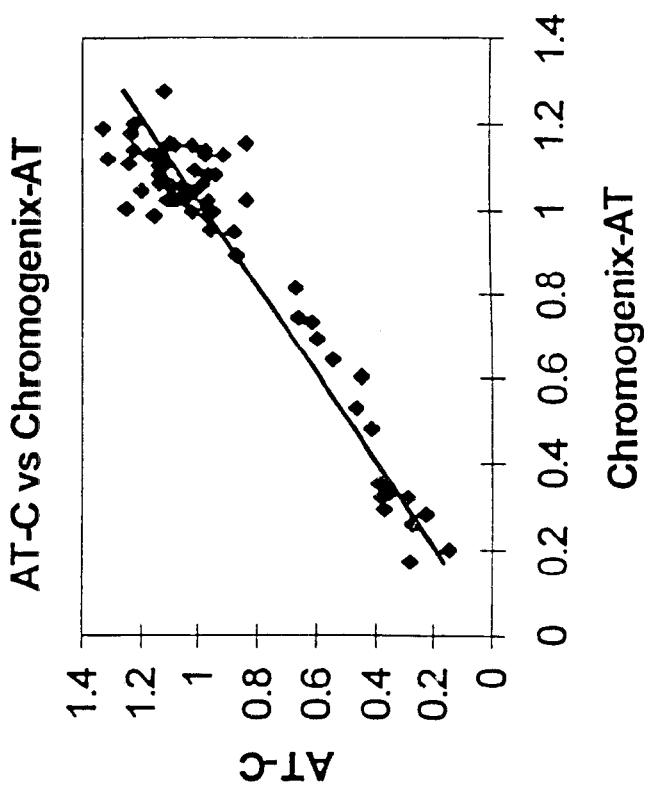
FIG. 1 depicts a graphical comparison and correlation between the results obtained from an assay performed according to the present invention (AT-C) and an amidolytic-based activity assay performed according to the chromogenic AT assay from Chromogenix (Chromogenix-AT).

The present invention provides a simple one-stage in vitro method for measuring AT activity levels in any sample containing AT. The invention therefore can be used to measure AT activity levels in samples from patients such as plasma or serum to detect a deficiency of AT activity or to monitor antithrombin therapy using antithrombin concentrates The invention can also be used to monitor the level of AT during production procedures such as cell culture or during purification of AT from plasma or culture fluid. If protease inhibitors other than AT are present at greater than physiological concentrations, controls must be run to determine the effect of these other inhibitors on the assay. Such controls may include testing the vehicle (plasma, culture fluid or buffer solution that is being tested for AT activity) in the absence of AT at dilutions equivalent to those used for the assay of AT, as well as the addition of a known quantity of AT to the vehicle and calculating its recovery.

In carrying out the method, a diluted test sample is mixed with an AT deficient substrate plasma, an activator of the contact phase of the intrinsic coagulation pathway and a phospholipid. An activated partial thromboplastin time (APTT) reagent may also be used to provide the contact phase activator and the phospholipid to the reaction mixture. An AT-augmenting compound, if not present in the AT-deficient substrate plasma is also added to the test sample. A calcium ion containing solution is then added and the clotting time determined by mechanical or optical means.

The term contact phase refers to that part of the intrinsic coagulation pathway which does not require calcium ions for activation and which is presently understood to include the activation of factor XII, prekallikrein, kininogen and factor XI. Contact phase activators are known and include ellagic acid, silica and kaolin. The term APTT reagent is understood, and intended to refer to a reagent which contains at least a contact phase activator and a phospholipid. A phospholipid, which may be synthetic or plant or animal tissue extract derived, is required to support assembly of activated coagulation factor complexes by acting as a template. Different APTT reagents are widely available commercially. For optimal results, an APTT reagent which provides a clotting time of between 80 and 140 seconds for a dilution of reference plasma representing 100% AT activity, and between 40 and 60 seconds for a dilution of a reference plasma representing approximately 6.3% AT activity should be selected.

For optimum results, the reaction mixture, prior to the introduction of calcium ions is incubated at a time and temperature sufficient to activate the contact phase of the intrinsic coagulation pathway, typically, for about 2 to 30 minutes at a temperature of about 20 to 40° C. An optimal incubation time and temperature may vary depending on the APTT reagent selected, and in some cases, may not be necessary provided the variability in the clotting time is within an acceptable limit for the particular application of the assay.

The calcium ions may be introduced to the mixture by addition of calcium salt solution with a stock concentration between 0.01 and 0.1 M. The optimal calcium concentration is that which provides the shortest clotting time and may be determined by titration. The final concentration of calcium ions in the clotting mixture which the inventors have found optimal is between 4 and 10 mM. For example, one volume of 0.02 M calcium chloride solution may be added to a three volume reaction mixture to achieve a concentration of 5 mM.

The optimal dilution range of the test sample which may vary depending on the APTT reagent sensitivity and the instrumentation used, can be readily determined by those skilled in the art. The inventors have generated a reference curve using reference plasma dilutions of 1/10, 1/20, 1/40, 1/80, 1/160 representing AT concentrations of approximately 100%, 50%, 25%, 12.5% and 6.3%, respectively, referenced against a World Health Organization (W.H.O.)-traceable calibrator.

The substrate plasma used in this method is an AT-deficient plasma that may be prepared by the known methods including immuno-affinity chromatography, or affinity chromatography using immobilized sulphated polysaccharides such as heparin as previously described (Hoogendoorn, 1980), or some combination of these techniques, to remove AT while retaining the coagulation factor activities of intrinsic coagulation. To ensure that the only component influencing the clotting time is due to the level of AT in the test sample, other factors which may influence the clotting time should be present in sufficient concentrations in the AT-deficient substrate plasma to minimize any influence of small and variable quantities present in the test sample. An AT-deficient substrate plasma for use in the invention should therefore have a normal clotting time in an ATPP based assay, in the absence of an AT augmenting compound such as heparin described below.

For optimum results, the substrate plasma should contain less than about 1% of normal AT levels as determined by an assay method that can accurately detect AT levels of less than 2%, for example, an antigen assay or an activity assay. The substrate plasma should contain normal levels of other coagulation inhibitors such as heparin cofactor II, $\alpha_2$-macroglobulin and $\alpha_1$-antitrypsin. Additionally, optimum results may be obtained when at least 40% of normal activity levels of coagulation factors XII, XI, IX, VIII, X, V and II as measured by a one-stage clotting activity assay, and at least 1 gram per liter of fibrinogen are present in the substrate plasma. Normal activity levels of coagulation factors and coagulation inhibitors refer to those determined from a WHO traceable standard.

An AT-augmenting compound as that term is used in this invention is a compound capable of prolonging the APTT of normal plasma but not of AT-deficient plasma. For the purposes of this invention, a prolongation of the APTT of less than 20 seconds is not considered significant. An AT augmenting compound is most typically heparin or a heparin derivative, but also includes other sulphated compounds such as a glycosaminoglycan, a sulphated oligosaccharide or a polysulphone.

The AT-augmenting compound may be added to the AT-deficient substrate plasma or mixed directly with the test sample either before or at the time of introducing calcium ions to the mixture. In the case of heparin, optimum results may be achieved with an AT-deficient plasma which has an APTT in the normal range and which increases by less than 20 seconds in the presence of heparin. Yet still, optimum results may be achieved when heparin is present in a concentration sufficient to prolong the APTT by 2- to 4-fold in the presence of diluted AT in the test sample and such concentration is typically in the range of 0.5 to 2 international units per milliliter, or 2.5 to 10 micrograms per milliliter. Addition of small amounts of AT in the diluted sample, when mixed with heparin or with the substrate plasma containing heparin, causes a substantial and dose dependent increase in the clotting time when an APTT reagent is added.

In one specific embodiment, one volume of AT deficient substrate plasma is mixed with one volume of test or reference sample diluted 1/10 and then mixed with one volume of APTT reagent. The sample is diluted using a buffer such as 0.01 to 0.1 M imidazole, Tris or HEPES or other suitable buffers known in the art. The mixture is incubated at 37° C. for 180 seconds at which time one volume of 20 mM $CaCl_2$ is added and the clot time recorded. The clotting time is then compared to the clotting times of a reference plasma (such as a WHO traceable reference) containing a known amount of AT to obtain a measure of the AT activity in the test sample. For this comparison, a reference curve can be generated using different dilutions of the reference plasma. A typical curve may include readings from reference plasma diluted 1:10, 1:20, 1:40, 1:80 ad 1:160, representing AT activity levels of 100, 50, 25, 12.5 and 6.5%, respectively, referenced against a WHO traceable calibrator.

The present method is easy and relatively quick to perform in that it requires no pre-treatment of samples, such as defibrination. Additionally, there is no requirement for specialized detection equipment, as the results may be read manually. As the method can be performed on most all automated or semi-automated coagulation analysers, it may be automated using existing laboratory instrumentation and software.

The method of the invention measures the activity of AT on a wider range of endogenously generated coagulation factors than that possible for the prothrombin time method disclosed in Enomoto. As such, the present method is believed to provide a better measure of the physiological AT activity in vivo. Furthermore, given the greater sensitivity of the inhibition of the intrinsic coagulation activation to heparin (Nordfang et al, 1993 Thrombosis and Haemostasis 70 (3) 448–453), relatively low levels of heparin can be used. The present method therefore avoids the reduced efficiency of inhibition by AT that can occur at higher heparin concentrations.

Table 1 below shows typical APTT clot times obtained according to the invention for a reference plasma and for known normal control and known abnormal control plasmas.

TABLE 1

| Sample | Dilution | Clotting time (sec) | Value obtained |
|---|---|---|---|
| Reference plasma (AT value of 96%) | 1:10 | 86.2" | NA |
| | 1:20 | 67.9" | |
| (CCNRP #7020, Precision Bio-Logic) | 1:40 | 58.2" | |
| | 1:80 | 52.3" | |
| $R^2 = 0.9987$ | 1:160 | 48.9" | |
| Normal plasma | 1:20 | 68.3" | Mean = 102% |
| (NP97-05 Precision BioLogic) | 1:40 | 59.1" | |
| Abnormal plasma | 1:20 | 53.4" | Mean = 32% |
| (ARPI #8020, Precision BioLogic) | 1:40 | 50.1" | |

With reference to FIG. 1, the results of the present method (AT-C assay) correlate well with the results obtained with the currently popular amidolytic based activity and further demonstrates the specificity of the method according to the invention.

Moreover, as shown below in Table 2, no significant difference is seen between results of the two methods for test samples from patients receiving heparin therapy. These results further demonstrate that the method of present invention is as specific as the currently popular method. Data are reported as AT units per milliliter using a WHO reference plasma containing known amounts of AT as a reference calibrator.

TABLE 2

| Sample | AT-C Assay (U/mL) | Chromogenix AT assay (U/mL) |
|---|---|---|
| H58 | 0.64 | .76 |
| H71 | .83 | 0.91 |
| Hep 1 | .62 | 0.8 |
| Hep 2 | 0.75 | 0.78 |
| Hep 3 | .76 | 0.72 |
| Hep 8 | 1.1 | 1.07 |
| Hep 9 | 0.85 | 0.8 |
| Hep 10 | 0.85 | 0.83 |
| Hep 11 | 1.16 | 0.96 |
| Hep 12 | 0.71 | 0.7 |
| Hep 9.1 | 0.59 | 0.61 |
| Hep 10.1 | 0.76 | 0.7 |
| Hep Brown | 0.73 | 0.98 |
| Hep 70 | 0.83 | 0.84 |
| Hep EVA | 0.53 | 55 |
| Hep 58 | 0.82 | 0.82 |
| 1003HC49 | 0.84 | 1.01 |
| Hep 40 | 0.54 | 0.67 |
| Hep Mou | 0.59 | 0.81 |
| Hep 7 | 0.75 | 0.73 |
| Hep 50 | 0.83 | 0.84 |
| MEAN | 0.77 | 0.77 |
| Standard Deviation | 0.16 | 0.16 |

Table 3 shown below illustrates the effect of addition of heparin cofactor II (HCII) to HCII immune-deficient plasma at a concentration gradient of 0 to 200% of normal concentration. The AT activity of the resulting plasmas as measured according to the invention changed less than 10% even at high HCII concentration demonstrating that the present method is insensitive to interference from other coagulation inhibitors. It is believed that dilution of the test plasma and the use of a substrate plasma with normal levels of these inhibitors minimizes the effect of modest additions of these inhibitors from the reference or test plasmas on the clotting time endpoint. The specificity may also be attributed to the wide spectrum of coagulation enzymes inhibited by AT in the present method.

TABLE 3

| Sample | Relative HCII (%) | Dilution | AT-C assay value |
|---|---|---|---|
| HCII-DP alone | <1% | 1:20 | 140% |
| HCII-DP + 25 µg/ml purified HCII | 50% | 1:20 | 144% |
| HCII-DP + 50 µg/ml purified HCII | 100% | 1:20 | 136% |
| HCII-DP + 100 µg/ml purified HCII | 200% | 1:20 | 138% |

The present method is sensitive to AT activity levels as low as 12% of the normal activity. Moreover, no interference has been observed in plasma samples from patients on coumadin therapy or on heparin therapy or with lupus anticoagulant inhibitors.

The reagents of the present method may be conveniently packaged and the invention therefore also contemplates a kit for determining AT activity levels. For ease of packaging and storage, the substrate plasma in the kit may be lyophilized. In this instance, the kit may include a diluent for dissolving the lyophilized substrate plasma. The diluent may be any suitable buffer for example containing about 0.01 to 0.1 M imadazole, Tris or HEPES or other suitable buffers as would be known to a skilled person in the art, including buffers described by Good et al (Biochemistry 5 (1966), pp.467). The kit may also include a reference or control plasma which may also be lyophilized.

One skilled in the art can readily appreciate that various modifications can be made to the described embodiments without departing from the scope and spirit of the invention. Such modifications are also intended to be within the scope of the invention.

We claim:

1. A method for determining antithrombin activity in a sample comprising:
   mixing in a reaction mixture a dilution of the sample with an antithrombin deficient plasma, an activator of contact phase of intrinsic coagulation pathway, a phospholipid and an antithrombin augmenting compound wherein said antithrombin deficient plasma comprises intrinsic coagulation enzymes;
   introducing calcium ions to the reaction mixture;
   measuring coagulation time; and
   comparing the coagulation time to a reference standard.

2. The method according to claim 1 further comprising the step of incubating the sample with the antithrombin deficient plasma and the activator of contact phase prior to mixing with the phospholipid and the antithrombin augmenting compound.

3. The method according to claim 1 wherein the antithrombin augmenting compound is heparin.

4. The method according to claim 3 further comprising the step of incubating the reaction mixture prior to introducing calcium ions.

5. The method according to claim 4, wherein the mixture is incubated for about 2 to 30 minutes at a temperature of about 20 to 40° C.

6. The method according to claim 5, wherein the mixture is incubated for about 3 to 5 minutes at 37° C.

7. The method according to claim 4, wherein the antithrombin deficient plasma comprises less than 1% of normal antithrombin level.

8. The method according to claim 7, wherein the antithrombin deficient plasma comprises at least 40% normal activity levels of the intrinsic coagulation enzymes.

9. The method according to claim 8, wherein heparin is present in the reaction mixture at a concentration of about 2.5 to 10 µg/ml.

10. The method according to claim 9, wherein the antithrombin deficient plasma comprises at least about 1 mg/ml of fibrinogen.

11. The method according to claim 10 wherein the sample is mixed with the activator and the phospholipid by addition of an APTT reagent.

12. The method according to claim 11, wherein the calcium ions are introduced by adding calcium chloride solution to the mixture.

13. The method according to claim 12, wherein the calcium chloride solution is at a concentration of about 0.015 to 0.03 M.

14. The method according to claim 13, wherein the calcium chloride solution is at a concentration of about 0.02 M.

15. The method according to claim 14, wherein the sample is plasma of a patient.

16. The method according to claim 15, wherein the patient is receiving antithrombin therapy.

17. A method for determining antithrombin activity in a sample comprising:
    mixing in a reaction mixture a dilution of the sample with an antithrombin deficient plasma, an activator of contact phase of intrinsic coagulation pathway and a phospholipid wherein said antithrombin deficient plasma comprises intrinsic coagulation enzymes and an antithrombin augmenting compound;
    introducing calcium ions to the reaction mixture;
    measuring coagulation time; and
    comparing the coagulation time to a reference standard.

18. The method according to claim 17, wherein the antithrombin augmenting compound is heparin.

19. The method according to claim 18 further comprising the step of incubating the reaction mixture prior to introducing calcium ions.

20. The method according to claim 19, wherein the mixture is incubated for a period of about 2 to 30 minutes at a temperature of about 20 to 40° C.

21. The method according to claim 20, wherein the mixture is incubated for about 3 minutes at 37° C.

22. The method according to claim 19, wherein the antithrombin deficient plasma comprises less than 1% of normal antithrombin level.

23. The method according to claim 22, wherein the antithrombin deficient plasma comprises at least 40% normal activity levels of the intrinsic coagulation enzymes.

24. The method according to claim 23, wherein heparin is present in the reaction mixture at a concentration of about 2.5 to 10 µg/ml.

25. The method according to claim 24, wherein the antithrombin deficient plasma comprises at least about 1 mg/ml of fibrinogen.

26. The method according to claim 25 wherein the sample is mixed with the activator and the phospholipid by addition of an APTT reagent.

27. The method according to claim 26, wherein the calcium ions are introduced by adding calcium chloride solution to the mixture.

28. The method according to claim 27, wherein the calcium chloride solution is at a concentration of about 0.015 to 0.03 M.

29. The method according to claim 28, wherein the calcium chloride solution is at a concentration of about 0.02 M.

30. The method according to claim 29, wherein the sample is plasma of a patient.

31. The method according to claim 30, wherein the patient is receiving antithrombin therapy.

32. A kit for determining antithrombin activity in a sample comprising:
    an antithrombin-deficient plasma wherein the plasma comprises intrinsic coagulation enzymes;
    an antithrombin augmenting compound;
    an APTT reagent; and
    calcium salt solution.

33. The kit according to claim 32 wherein the antithrombin augmenting compound is heparin.

34. The kit according to claim 33, wherein the heparin is present in the antithrombin deficient plasma.

35. The kit according to claim 34, wherein the plasma is lyophilised.

36. The kit according to claim 35 further comprising a diluent.

37. The kit according to claim 32 further comprising a reference plasma.

38. The kit according to claim 32 further comprising a control plasma.

* * * * *